United States Patent [19]

Gatenby

[11] Patent Number: 4,957,481
[45] Date of Patent: Sep. 18, 1990

[54] PHOTODYNAMIC THERAPEUTIC TECHNIQUE

[75] Inventor: Robert A. Gatenby, Wynnewood, Pa.

[73] Assignee: U.S. Bioscience, Blue Bell, Pa.

[21] Appl. No.: 374,823

[22] Filed: Jul. 3, 1989

Related U.S. Application Data

[63] Continuation of Ser. No. 103,319, Oct. 1, 1987, abandoned.

[51] Int. Cl.⁵ .............................................. A61N 1/30
[52] U.S. Cl. ..................... 604/20; 128/665; 604/49; 606/10
[58] Field of Search ................. 604/20, 49; 128/665, 128/303.1, 241; 606/29, 2, 10

[56] References Cited

U.S. PATENT DOCUMENTS

| | | | |
|---|---|---|---|
| 3,860,006 | 1/1975 | Patel | 128/347 |
| 4,512,762 | 4/1985 | Spears | 604/21 |
| 4,541,438 | 9/1985 | Parker et al. | 128/664 |
| 4,577,636 | 3/1986 | Spears | 128/654 |
| 4,610,241 | 9/1986 | Gordon | 128/1.3 |
| 4,612,938 | 9/1986 | Dietrich et al. | 128/665 |
| 4,634,557 | 1/1987 | Sato | 540/145 |
| 4,817,601 | 4/1989 | Roth et al. | 128/303.1 |
| 4,822,335 | 4/1989 | Kawai et al. | 604/20 |
| 4,836,203 | 6/1989 | Müller et al. | 128/203.1 |
| 4,889,129 | 12/1989 | Dougherty et al. | 128/664 |

OTHER PUBLICATIONS

Tombs and Sandler, Computed Tomography in Trauma, 1/87, 60–61, 126–128.

*Primary Examiner*—C. Fred Rosenbaum
*Assistant Examiner*—Mark O. Polutta
*Attorney, Agent, or Firm*—Wegner & Bretschneider

[57] ABSTRACT

The present invention is directed toward methods for the reduction of the severity of symptoms resulting from tumors, such as pain induced by the pressure exerted on a nerve by the tumor mass. Additionally, methods for the reduction of tumor size are also contemplated.

27 Claims, No Drawings

PHOTODYNAMIC THERAPEUTIC TECHNIQUE

This application is a continuation of U.S. application Ser. No. 103,319, filed Oct. 1, 1987, now abandoned.

BACKGROUND OF THE INVENTION

The present invention is related to a photodynamic therapy technique useful in the treatment of tumors and their related symptoms.

Lipson et al., *J.N.C.I.*, vol. 26, pp. 1-8 (1961) discussed that fluorescence of human tumors can be accomplished by systemic injection of HpD. Dougherty et al., *J.N.C.I*, vol. 55, pp. 115-119 (1975) discussed the combination of systemic administration of HpD and exposure to red light emitted by a xenon arc lamp in the treatment of a transplanted murine mammary tumor. Also, Lipson et al., *Cancer*, vol. 20, pp. 2255-57 (1967) involved the use of intravenous administration of HpD and exposure to filtered light from a xenon arc lamp in the treatment of a human breast tumor.

However, such treatment methods had several disadvantages including:

(1) increased photosensitivity to sunburn resulting from deposition of HpD in the skin;

(2) insufficient accumulation of HpD in large tumors;

(3) poor light transmission through tumors due to clotting and carbonization of blood onto the diffusing surface of the fiberoptic; and (4) necessity of surgical exposure for deep tumors.

SUMMARY OF THE INVENTION

The present invention is directed toward methods for the reduction of the severity of symptoms resulting from tumors such as pain induced by the pressure exerted on a nerve by the tumor mass which avoid the complications set forth above. Additionally, methods for the reduction of tumor size are also contemplated.

DETAILED DESCRIPTION OF THE INVENTION

The first aspect of the present invention involves a method of reducing the severity of symptoms resulting from the presence of a tumor in a subject comprising:

(1) injection of an effective amount of a photosensitive compound directly into said tumor in at least one location in said tumor;

(2) insertion of at least one sheathed light source into said tumor capable of emitting light at a wavelength which is absorbed by said photosensitive compound; and (3) activation of said light source whereby said light is absorbed by said photosensitive compound thereby disrupting the tumor cells and reducing the severity of tumor-induced symptoms.

As a photosensitive compound of the present invention there is contemplated any compound exhibiting an oxidative or other reactive response which would result in oxidation of tumor cells or an increase in the temperature of the surrounding tumor tissue upon exposure of the photosensitive compound to light. Exemplary of such compounds are hematoporphyrin derivative HpD, chlorins, phthalocyanines, bacteriochlorins, merocyanine 540 and methylene blue. In a preferred embodiment of this aspect of the present invention, the photosensitive compound is hematoporphyrin derivative HpD, As an effective amount of the photosensitive compound of the present invention, there is contemplated an amount sufficient to achieve a reduction in the severity of symptoms resulting from the presence of a tumor in a subject. Such a reduction in tumor-induced symptoms can be achieved through the administration of an amount of photosensitive compound in excess of about 5 micrograms/g of tumor tissue. Generally, as the dose of the photosensitive compound increases, the effectiveness of a given amount of applied light will increase. However, this is believed to hold true only for doses of up to about 150 micrograms/g of tumor tissues. Increases significantly above this level may not lead to increased benefits.

The administration of photosensitive compound may be accomplished through a single direct administration to the tumor mass. Preferably, the single administration is accomplished through intratumoral administration as close to the center of the tumor mass as possible. This direct, local administration permits the use of higher doses than are possible with I.V. administration. I.V. doses are generally about 1 microgram/g of tumor, which is usually not adequate. I.V. administration to higher levels, such as those set forth above, would most likely result in toxicity problems.

To improve the diffusion of the photosensitive compound within the tumor, multiple direct administrations of the compound may be undertaken. For example, 0.5 ml of a solution containing a photosensitive compound can be injected at each injection site, wherein each injection site is separated by 1-2 cm on the surface of the tumor mass.

Exemplary tumors which may be treated by the process of the present invention include adenocarcinoma, leiomyosarcoma and squamous cell carcinoma located in various areas of the body of the subject such as the presacral mass, inguinal nodes, cervical nodes, acetabulum, paraspinal mass, bone and brain. The technique is effective in the treatment of large, deep tumors without the necessity for surgically exposing such tumors.

As the light source of the present invention there is contemplated any light source capable of the following:

(1) emission of light of a wavelength which is absorbed by the photosensitive compound;

(2) insertion to the body without induction of toxic responses; and (3) insertion in combination with a sheath.

Exemplary of such light sources are fiberoptic light sources such as lasers.

With respect to requirement (1) recited above, it is preferable that the light source emit light of a wavelength which corresponds to a wavelength of peak absorption of the photosensitive compound used. For example, when the hematoporphyrin derivative HpD is used as the photosensitive compound, one light wavelength which may be emitted by the light source is 630 nm.

The light source(s) of the present invention are sheathed to prevent the clotting and carbonizing of blood thereon during the treatment process. Preferably, the sheaths utilized in the method of the present invention are those which do not hinder the transmission of light. Thus, preferred embodiments of this aspect of the invention involve the sheathing of the light source in a clear, sheath catheter. Also preferred is the sheathing of the light source in a teflon catheter.

Similar to the multiple administration of the photosensitive compound, multiple light sources could be inserted into the tumor mass to provide light to the photosensitive compound. Alternatively, a single light source could be inserted into the tumor mass, activated, moved to another location in the tumor mass, activated, etc. Combinations of both of these techniques are also contemplated by the present invention.

The injection, insertion and activation steps of the present invention may be accomplished manually, under computed tomographic guidance or any combination thereof.

A second aspect of the present invention involves a method of reducing the size of a tumor present in a subject comprising:

(1) injection of an effective amount of a photosensitive compound directly into said tumor in at least one location in said tumor;

(2) insertion of at least one sheathed light source into said tumor capable of emitting light at a wavelength which is absorbed by said photosensitive compound; and (3) activation of said light source whereby said light is absorbed by said photosensitive compound thereby disrupting the tumor cells and reducing the size of said tumor.

As a photosensitive compound of the present invention there is contemplated any compound exhibiting an oxidative or other reactive response which would result in an increase in the temperature of the surrounding tumor tissue upon exposure of the photosensitive compound to light. Exemplary of such compounds are hematoporphyrin derivative HpD, chlorins, phthalocyanines, bacteriochlorins, merocyanine 540 and methylene blue. In a preferred embodiment of this aspect of the present invention, the photosensitive compound is hematoporphyrin derivative HpD.

As an effective amount of the photosensitive compound of the present invention, there is contemplated an amount sufficient to achieve a reduction in the side of a tumor in a subject. Such a reduction in tumor size can be achieved through the administration of an amount of photosensitive compound in excess of about 5 micrograms/g of tumor tissue. Generally, as the dose of the photosensitive compound increases, the effectiveness of a given amount of light will increase. However, this is believed to hold true only for doses of up to about 150 micrograms/g of tumor tissues. Increases significantly above this level may not lead to increased benefits.

Most of the photosensitive compounds contemplated by the present invention are known compounds which can be obtained by known methods or from their manufacturers. Others are merely commercially available compounds which are modified or purified by simple chemical procedures. For example, commercially available HpD (which may be prepared according to the process described in U.S. Pat. No. 2,858,320 assigned to Baxter Labs, incorporated herein by reference) may be subjected to acetylation and hydroxylation steps prior to use in the present invention. These compounds are preferably administered by injection of a saline solution of the compounds directly into the tumor mass of the patient.

The administration of photosensitive compound may be accomplished through a single direct administration to the tumor mass. Preferably, the single administration is accomplished through intratumoral administration as close to the center of the tumor mass as possible.

To improve the diffusion of the photosensitive compound within the tumor, multiple direct administrations of the compound may be undertaken. For example, 0.5 ml of a solution containing a photosensitive compound can be injected at each injection site, wherein each injection site is separated by 1-2 cm on the surface of the tumor mass.

Exemplary tumors which may be treated by the process of the present invention include adenocarcinoma, leiomyosarcoma and squamous cell carcinoma located in various areas of the body of the subject such as the presacral mass, inguinal nodes, cervical nodes, acetabulum, paraspinal mass, and bone. The technique is effective in the treatment of large, deep tumors without the necessity for surgically exposing such tumors.

As the light source of the present invention there is contemplated any light source capable of the following:

(1) emission of light of a wavelength which is absorbed by the photosensitive compound;

(2) insertion to the body without induction of toxic responses; and (3) insertion in combination with a sheath.

Exemplary of such light sources are fiberoptic light sources such as lasers.

With respect to requirement (1) recited above, it is preferable that the light source emit light of a wavelength which corresponds to a wavelength of peak absorption of the photosensitive compound used. For example, when the hematoporphyrin derivative HpD is used as the photosensitive compound, one light wavelength which may be emitted by the light source is 630 nm.

The light source(s) of the present invention are sheathed to prevent the clotting and carbonizing of blood thereon during the treatment process. Preferably, the sheaths utilized in the method of the present invention are those which do not hinder the transmission of light. Thus, preferred embodiments of this aspect of the invention involve the sheathing of the light source in a clear, sheath catheter. Also preferred is the sheathing of the light source in a catheter made of a fluorinated polymer such as TEFLON.

Similar to the multiple administration of the photosensitive compound, multiple light sources could be inserted into the tumor mass to provide light to the photosensitive compound. Alternatively, a single light source could be inserted into the tumor mass, activated, moved to another location in the tumor mass, activated, etc. Combinations of both of these techniques are also contemplated by the present invention.

The activation time of the light source in the activation step varies on a case by case basis. In fact, the treatment time and energy application therein is influenced by tumor size and patient tolerance. For example, treatment times ranging between 15 and 80 minutes with a total energy application varying between 900–4800 Joules may be used. Generally, the optimal total energy applied can be about 100–150 Joules/cc of tumor.

The injection, insertion and activation steps of the present invention may be accomplished manually, under computed tomographic guidance or any combination thereof.

The following are exemplary of the present invention.

EXAMPLE I

Preparation of HpD

Commercially available hematoporphyrin (available from, for example, Porphyrin Products of Logan, Utah) is acetylated by continuously stirring the hematoporphyrin in admixture with weak acetic acid and sulfuric acid for 1 hour. The mixture is then dried and subjected to HPLC using a Zorbax ODS column (DuPont) and is eluted with aqueous tetrahydrofuran-acetate buffer (1:9). The resulting material is then exposed to dilute sodium hydroxide for 1 hour followed by purification by passage through a 0.22 micrometer filter in dimmed light. The product has a final concentration of HpD of 1.5 mg/ml and a pH of 7.00.

EXAMPLE II

Preparation of Mouse Test Subjects 12 week old Balb/cIcr mice are implanted with approximately $5 \times 10^6$ cells from a T-cell lymphoma in their flanks. Over 4 weeks the tumors are permitted to grow and achieve a diameter of 2–3 cm.

EXAMPLE III

Photosensitive Compound Diffusion in Tumors 12 tumors of Example II of 2.5–3.0 diameter (volume of 9–12 cm$^3$) are injected with HpD prepared according to Example I such that the concentration of HpD in the tumors is 100 micrograms/g of tumor tissue. This injection is done slowly into the center of the tumor. The mice are randomly killed at 1.5, 3.0 and 4.5 days following the injection and the diffusion of HpD is examined with a fluorescent microscope after the tumors are sectioned.

At 1.5 days, approximately 75% of the tumor volume exhibits fluorescence. At 3.0 and 4.5 days, 100% of the tumor volume exhibits fluorescence. Other body organs, such as the liver, spleen and kidneys exhibit minimal fluorescence at 1.5, 3.0 and 4.5 days.

EXAMPLE IV

Light Transmission in Tumors 16 mice with tumors prepared in accordance with Example II ranging from 2.5–3.0 cm in diameter are randomly assigned to 4 groups:

two groups in which HpD is injected 3 days before the experiment, one in which the laser fiberoptics are placed by means of sheath catheters and one in which the fiberoptics are placed without such catheters; and two groups in which no HpD is injected, subdivided in the same manner as above with respect to the sheathing of the fiberoptics.

The fiberoptics are paced into the tumors such that they are 12 mm from the edge of the tumor. The tumor edge is then place against the sensitive area of a digital photometer probe (Tektronix) which is calibrated to measure flux in radiation between 250–1200 nm with accuracy of +5%. These measurements are taken in a dark room. The results of this experiment are shown in FIG. 1. Light transmission was increased by the presence of a sheath and the presence of HpD.

EXAMPLE V 50 mice of Example II with tumors 2.0-3.0 cm in diameter are randomly assigned to one of four groups.

(1) A control group, in which 0.5 ml of normal saline is injected into the center of each tumor. After 72–96 hours, a sheath catheter is placed in the tumor, but no laser light is applied.

(2) An HpD-only group, in which HpD (100 micrograms/g of tumor) is injected into the center of each tumor. After 72–96 hours, a clear/ sheath teflon catheter (Cook) is placed in the tumor, but no laser light is applied.

(3) A laser-only group, in which 0.5 ml of normal saline is injected into the center of each tumor. After 72–96 hours, a clear, sheath catheter is inserted into the tumor. The fiberoptics are then placed into the sheath, and laser light at 630 nm was applied (1.0 W average power with a total treatment time of 15 minutes, for a total energy of 900 J). The light is supplied by a tunable red-dye laser (Cooper Lasersonics) driven by a 6-W argon laser.

(4) An HpD and laser group, in which HpD (100 micrograms/g of tumor) is injected into the center of each tumor. After 72–96 hours, a sheath catheter is placed in the tumor and laser light is applied as in group (3).

The results of this experiment are shown in FIG. 2. Tumor volume is decreased in those mice of group (4).

EXAMPLE VI 10 human patients with tumors and suffering from pain induced by the tumors are selected for testing. The skin located directly over the tumor is located by computer tomography (CT) and HpD prepared in accordance with Example I is injected into multiple sites within the tumor by means of a 22-gauge needle. Approximately 0.5 ml of HpD is injected into the 5 injection sites located 1–2 cm apart on the tumor surface. A dose suitable to achieve an approximate concentration of 100 micrograms/g of tumor tissue is injected in all cases.

3–6 days after HpD injection, a 5-F, Teflon, clear sheath catheter (Cook) is inserted under CT guidance through the diameter of the tumor. The stylet is removed and approximately 0.5 ml of sterile heparinized saline solution is injected into the catheter. Next the laser fiberoptics are placed into the catheter. Laser light at 630 nm is applied according to tumor size.

In large tumors, the diffusing surface of the fiberoptics is initially inserted into the end of the catheter and the area of the tumor is treated for 30–35 minutes. The fiberoptics are then pulled back about 3 cm within the sheath so that a second area of the tumor is treated for another 30–35 minutes.

In smaller tumors, only the first (or a portion of the first) stage of the treatment for large tumors set forth above is utilized.

The laser fiberoptics are removed from the sheath and the sheath is removed from the subject with continuous application of a 50 ml syringe to aspirate any necrotic debris, if any resulting from the treatment. The results of the experiments obtained from interviews and CT scans after 4 weeks are presented in Table 1.

TABLE 1

| Tumor Type | Tumor Size (cm) | Tumor Symptom | Energy Exposure (J) | Symptomatic Relief | Change in Size |
| --- | --- | --- | --- | --- | --- |
| Adreno-carcinoma/rectum | 3 × 3 × 5 | Pain* | 900 | Complete | 20% reduction |
| Squamous Cell/penis | 4 × 4 × 5 | Leg edema w/ pain | 1020 | Leg Swelling Eliminated | 70% reduction |
| Squamous Cell/nasopharynx | 6 × 6 × 8 | Pain* | 1500 | Marked Improvement | 20% reduction |
| Adreno-carcinoma/sigmoid | 5 × 5 × 5 | Pain* with Leg Weakness | 2100 | Moderate/pain Marked/strength | 20% reduction |
| Adreno-carcinoma/rectum | 7 × 7 × 8 | None | 2700 | N/A | 20%@ reduction |
| Leiomyo-sarcoma/maxillary sinus | 8 × 8 × 8 | Pain* | 4200 | No Improvement | None@ |
| Adeno-carcinoma/cecum | 6 × 6 × 6 | Pain* | 3600 | Marked Improvement | 30%@ reduction |
| Adeno-carcinoma/colon | 12 × 10 × 8 | Pain* | 4800 | Marked Improvement | 30%@ reduction |
| Adeno-carcinoma/lung | 7 × 4 × 5 | Pain* | 3600 | Moderate Improvement | 20% reduction |
| Squamous Cell/unknown | 4 × 4 × 5 | Leg edema with pain | 2100 | Marked Reduction/ swelling and pain | 50% reduction |

*Severe pain requiring at least three daily doses of morphine.
'Moderate improvement in pain, marked increase in leg strength.
@Remaining tumor markedly necrotic on CT scans.

What is claimed is:

1. A method of reducing the severity of symptoms resulting from the presence of a tumor in a subject comprising:
   (1) injection of an effective amount of a photosensitive compound directly into said tumor in at least one location in said tumor;
   (2) insertion of at least one sheathed light source, completely sheathed in a clear sheath catheter, into said tumor, said light source being capable of emitting light at a wavelength which is absorbed by said photosensitive compound; and
   (3) activation of said light source whereby said light is absorbed by said photosensitive compound, thereby disrupting the tumor cells and reducing the severity of tumor-induced symptoms.

2. A method of claim 1, wherein said insertion includes inserting a fiberoptic light source.

3. A method of claim 2, wherein said insertion includes inserting a laser.

4. A method of claim 1, wherein said light source emits at a wavelength corresponding to a wavelength of peak absorption of said photosensitive compound.

5. A method of claim 1, wherein said photosensitive compound is administered in an amount between about 5 and about 200 micrograms/g of tumor tissue.

6. A method of claim 1, wherein said photosensitive compound is administered in an amount between about 80 and about 120 micrograms/g of tumor tissue.

7. A method of claim 1, wherein said catheter is made of a fluorinated polymer.

8. A method of claim 1, wherein said photosensitive compound is hematoporphyrin derivative HpD.

9. A method of claim 8, wherein said light source emits a wavelength of about 630 nm.

10. A method of claim 1, wherein said tumor is a large, deep tumor.

11. A method of claim 1, wherein said injection is accomplished under computed tomographic guidance.

12. A method of claim 1, wherein said insertion is accomplished under computed tomographic guidance.

13. A method of claim 1, wherein said activation is accomplished under computed tomographic guidance.

14. A method of reducing the size of a tumor present in a subject comprising:
   (1) injection of an effective amount of a photosensitive compound directly into said tumor in at least one location in said tumor;
   (2) insertion of at least one sheathed light source into said tumor capable of emitting light at a wavelength which is absorbed by said photosensitive compound; and
   (3) activation of said light source whereby said light is absorbed by said photosensitive compound thereby disrupting the tumor cells and reducing the size of said tumor.

15. A method of claim 14, wherein said insertion includes inserting a fiberoptic light source.

16. A method of claim 15, wherein said insertion includes inserting a laser.

17. A method of claim 14, wherein said light source emits at a wavelength corresponding to a wavelength of peak absorption of said photosensitive compound.

18. A method of claim 14, wherein said photosensitive compound is administered in an amount between about 5 and about 200 micrograms/g of tumor tissue.

19. A method of claim 14, wherein said photosensitive compound is administered in an amount between about 80 and about 120 micrograms/g of tumor tissue.

20. A method of claim 14, wherein said insertion includes inserting a light source sheathed in a clear, sheath catheter.

21. A method of claim 20, wherein said catheter is made of a fluorinated polymer.

22. A method of claim 14, wherein said photosensitive compound is hematoporphyrin derivative HpD.

23. A method of claim 22, wherein said light source emits a wavelength of about 630 nm.

24. A method of claim 14, wherein said tumor is a large, deep tumor.

25. A method of claim 14, wherein said injection and said insertion is accomplished under computed tomographic guidance.

26. A method of claim 14, wherein said insertion is accomplished under computed tomographic guidance.

27. A method of claim 14, wherein said activation is accomplished under computed tomographic guidance.

* * * * *